United States Patent [19]
Misra

[11] Patent Number: 5,550,248
[45] Date of Patent: Aug. 27, 1996

[54] SUBSTITUTED STRYL HETEROCYCLIC AMIDO PROSTAGLANDIN ANALOGS

[75] Inventor: Raj N. Misra, Hopewell, N.J.

[73] Assignee: E.R. Squibb & Sons, Inc., Princeton, N.J.

[21] Appl. No.: 619,569

[22] Filed: Nov. 29, 1990

[51] Int. Cl.$^6$ .................................................. C07D 493/08
[52] U.S. Cl. .................. 548/236; 548/311.4; 548/200
[58] Field of Search ............................ 548/236, 336, 548/200, 311.4

[56] References Cited

U.S. PATENT DOCUMENTS

| | | | |
|---|---|---|---|
| 5,043,451 | 8/1991 | Ohtani | 546/293 |
| 5,100,889 | 3/1992 | Misra et al. | 548/200 |

FOREIGN PATENT DOCUMENTS

| | | | |
|---|---|---|---|
| 374952 | 6/1990 | European Pat. Off. | 548/200 |
| 391652 | 10/1990 | European Pat. Off. | 548/200 |

OTHER PUBLICATIONS

As Belo Bioorg Chem, 04.03.81–SU278256 (23 Nov. 1987)CO7c–177 CO7d–261/06.
Chem Abs. SA Selects: Prostaglandins Issue 12, 1988 108:198903m. Kuz'mitskii, B. B. et al.
CA Selects: Prostaglandins, Issue 12, 1988, 108:204363d, Lakhvich, F. A. et al.

*Primary Examiner*—Robert Gerstl
*Attorney, Agent, or Firm*—Burton Rodney

[57] ABSTRACT

Prostaglandin analogs useful in treating thrombotic and vasospastic disease having the structural formula wherein:

$C_mH_p$ is an alkylene chain wherein m is 0, 1, 2, or 3 and $p=(2\times m)-1$, except that when m is 0, p is also 0;

n is 0, 1, 2 or 3;

R is $CO_2R'$, $CH_2OH$, $CONHSO_2R^3$, $CONHR^4$, or $-CH_2-$5—tetrazolyl;

R' is hydrogen, alkyl, or alkali metal;

X is O or NH;

Y is —O—, a single bond or vinylene, except that Y cannot be —O— when n is 0;

and the remaining symbols are as defined in the specification.

10 Claims, No Drawings

1

SUBSTITUTED STRYL HETEROCYCLIC AMIDO PROSTAGLANDIN ANALOGS

FIELD OF THE INVENTION

This invention relates to prostaglandin analogs useful as thromboxane $A_2$ receptor antagonists.

BRIEF DESCRIPTION OF THE INVENTION

A compound of the formula

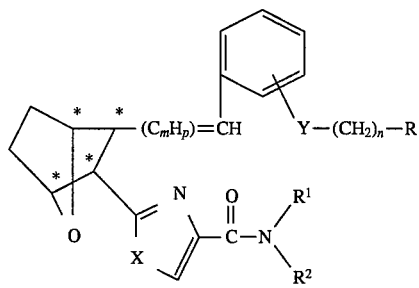

I is a thromboxane $A_2$ ($TXA_2$) receptor antagonist or a combined thromboxane $A_2$ receptor antagonist/thromboxane synthetase inhibitor. Compound I is useful, for example, in treating thrombotic or vasospastic disease with good duration of action. In compound I and throughout this specification, the symbols above are defined as follows:

$C_mH_p$ is an alkylene chain wherein m is 0, 1, 2, or 3 and p=(2×m)–1, except that when m is 0, p is also 0;

n is 0, 1, 2 or 3;

R is $CO_2R'$, $CH_2OH$, $CONHSO_2R^3$, $CONHR^4$, or —$CH_2$—5—tetrazolyl;

R' is hydrogen, alkyl, or alkali metal;

X is O or NH;

Y is —O—, a single bond or vinylene, except that Y cannot be —O— when n is 0;

$R^1$ is hydrogen, alkyl, alkenyl, alkynyl, aralkyl, aryl, cycloalkyl, cycloalkylalkyl, cycloheteroalkyl, cycloheteroalkylalkyl, heteroaryl or heteroarylalkyl, or amide

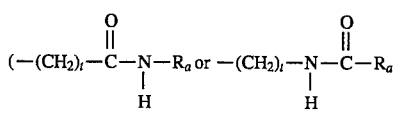

wherein t is 1 to 12 and $R_a$ is alkyl, aryl, cycloalkyl, or cycloalkylalkyl), each of $R^1$ being unsubstituted or optionally substituted with alkyl, aryl, cycloalkyl, or cycloalkylalkyl;

$R^2$ is hydrogen, alkyl, aryl, or aralkyl; or $R^1$ and $R^2$ together with the nitrogen to which they are linked may form a 5- to 8-membered ring;

$R^3$ is alkyl, aryl or aralkyl; and $R^4$ is hydrogen, alkyl, aryl, aryl or aralkyl.

Thus, the compounds of the invention include the following types of compounds, which are preferred:

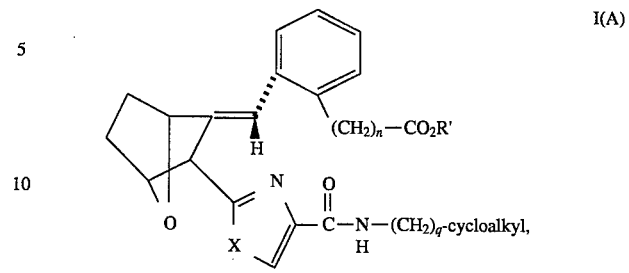

I(A)

wherein X, R', and n are as defined above and q is an integer from 1 to 7. Most preferred are those compounds wherein R' is hydrogen, q is 4, n is 2, and the cycloalkyl group is cyclohexane.

DETAILED DESCRIPTION OF THE INVENTION

Definition of Terms

The term "alkyl" includes both straight and branched chain radicals of up to 12 carbons, preferably 1 to 4 carbons, such as methyl, ethyl, propyl, isopropyl, butyl, t-butyl, isobutyl, pentyl, hexyl, isohexyl, heptyl, 4,4-dimethylpentyl, octyl, 2,2,4-trimethylpentyl, nonyl, decyl, undecyl, dodecyl, the various branched chain isomers thereof and the like, which may be substituted with one or two trifluoromethyl, halo or hydroxyl groups.

The term "cycloalkyl" includes saturated cyclic hydrocarbon groups containing 3 to 12 carbons, preferably 3 to 8 carbons, which include cyclopropyl, cyclobutyl, cyclopentyl, cyclohexyl, cycloheptyl, cyclooctyl, cyclodecyl and cyclododecyl.

The term "aryl" or "Ar" refers to monocyclic or bicyclic aromatic groups containing from 6 to 10 carbons in the ring portion, such as phenyl, naphthyl, which may include 1 or 2 substituents on either the phenyl or naphthyl such as alkyl, trifluoromethyl, halogen (Cl, Br, I or F), alkoxy, arylalkoxy, hydroxy, alkylthio, alkylsulfinyl, alkylsulfonyl, phenylthio, phenylsulfinyl and/or phenylsulfonyl.

The term "aralkyl" refers to alkyl groups as discussed above having an aryl substituent, such as benzyl.

The terms "alkoxy" and "aralkoxy" refer to the above alkyl and aralkyl groups linked to an oxygen atom.

The term "halogen" or "halo" refers to chlorine, bromine, fluorine or iodine, with chlorine being preferred.

The term "alkenyl" as employed herein with respect to the $R^1$ substituent includes a carbon chain of up to 12 carbons, preferably 3 to 10 carbons, having at least one double bond, which will be separated from "N" by at least one saturated carbon moiety such as —$(CH_2)_q$— where q can be 1 to 14, such as 2-propenyl, 2-butenyl, 3-butenyl, 2-pentenyl, 4-pentenyl and the like, and may include a halogen substituent such as I, Cl, or F.

The term "alkynyl" as employed herein with respect to the $R^1$ substituent includes a carbon chain of up to 16 carbons, preferably 3 to 10 carbons, having at least one triple bond, which will be separated from "N" by at least one saturated carbon moiety such as —$(CH_2)_q$— wherein q can be 1 to 14, such as 2-propynyl, 2-butynyl, 3-butynyl and the like.

The term "cycloheteroalkyl" as used herein as an $R^1$ substituent refers to 5-, 6- or 7-membered saturated rings that include 1 or 2 heteroatoms such as nitrogen, oxygen and/or sulfur, and which are linked to the "N" of the

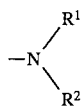

group through a carbon atom either beta or gamma to a heteroatom, such as

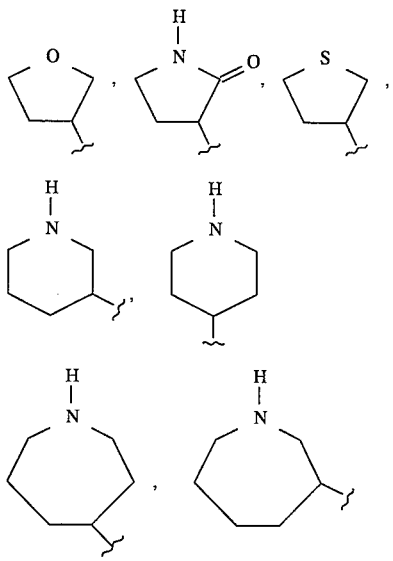

and the like.

The term "heteroaryl" or "heteroaromatic" as an $R^1$ substituent refers to 5- or 6-membered aromatic rings that include 1 or 2 heteroatoms such as nitrogen, oxygen or sulfur, which are not directly linked through a hetero atom to the "N" of the

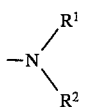

group, such as

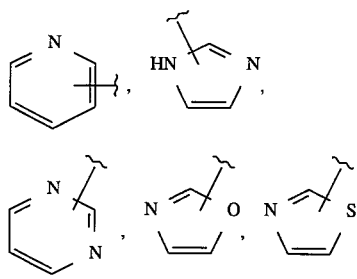

and the like.

The term "cycloheteroalkylalkyl" as used herein with respect to $R^1$ refers to 5-, 6- or 7-membered saturated rings that include 1 or 2 heteroatoms such as nitrogen, oxygen or sulfur, and are linked to the "N" of the

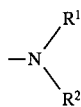

group through a $(CH_2)_x$ chain wherein x is 1 to 12, preferably 1 to 8, such as

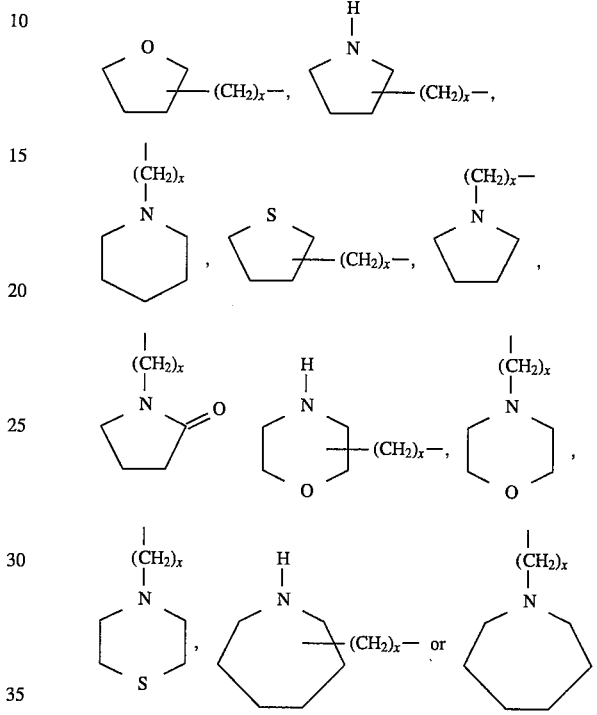

and the like.

The term "heteroarylalkyl" as used herein with respect to $R^1$ refers to 5-, 6- or 7-membered aromatic rings that include 1 to 4 nitrogen and/or 1 or 2 oxygen or sulfur atoms, and is linked to the "N" of the

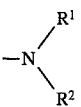

group through a $-(CH_2)_x-$ chain where x is 1 to 12, preferably 1 to 8, such as

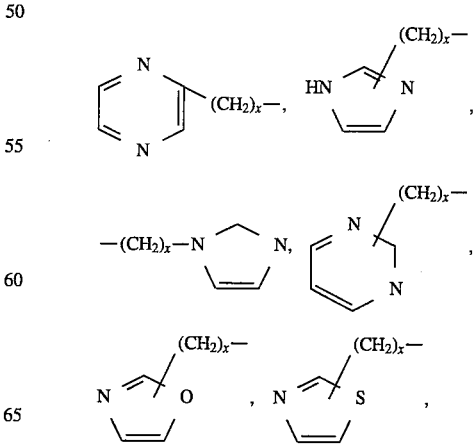

-continued

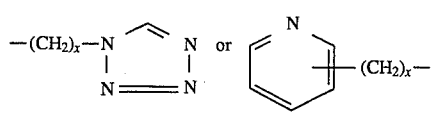

and the like.

Process of Preparation

Compounds of the invention wherein Y is a single bond and X is O are prepared starting with bromophenylalkyl alcohol A

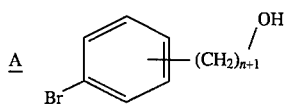

wherein n is 0, 1, 2, 3 or 4. Compound A is treated with a protecting compound (e.g., t-butylchloroiphenylsilane) in the presence of an amine base (e.g., triethylamine) and an inert solvent, employing conventional procedures, to form the protected bromophenylalkyl compound B

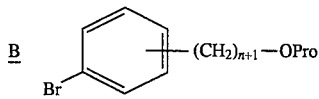

wherein Pro represents a protecting group. Examples of protecting compounds suitable for use herein in reacting with bromophenalkyl alcohol A include but are not limited to

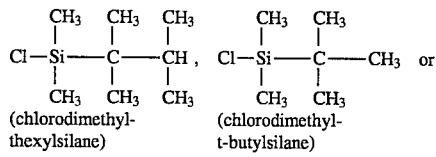

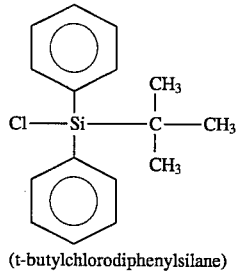

(t-butylchlorodiphenylsilane)

and the like.

The protected compound B then undergoes a metal-halogen exchange reaction by treatment with, for example, t—$C_4H_9Li$ or n—$C_4H_9Li$ in the presence of diethyl ether or tetrahydrofuran (THF) at about −100° to about 0° C., or is preferably subjected to a Grignard reaction by treatment with magnesium in the presence of an inert organic solvent (e.g., THF or diethyl ether) and then is condensed with (exo)octahydro-5,8-epoxy-1H-benzopyran-3-ol or (exo)octahydro-4,7-epoxyisobenzofuran-1-ol (prepared as described in U.S. Pat. No. 4,143,054) of the structure C

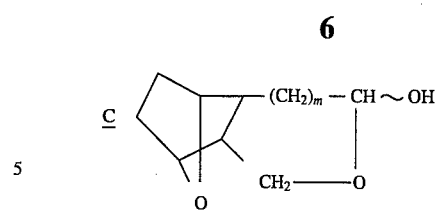

employing a molar ratio of C:B from about 1:2 to about 1:4, in the presence of an inert organic solvent such as THF at about −78° to about 25° C. to form the condensed 7-oxabicycloheptane compound

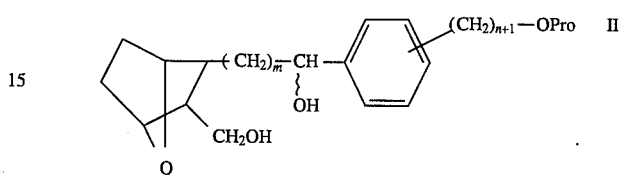

The primary hydroxyl group of compound II is protected by treatment with a protecting agent (e.g., t-butylchlorodiphenylsilane) in an organic solvent (e.g., methylene chloride) in the presence of a catalyst (e.g., dimethylaminopyridine) and a base (e.g., triethylamine) at about 20° to 30° C. to form

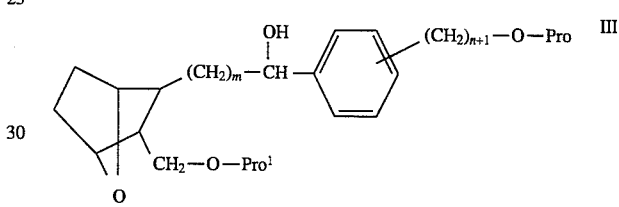

wherein $Pro^1$ is a protecting group. Exemplary protecting groups are those mentioned dove for Pro, but it is necessary that Pro and $Pro^1$ be different groups.

Alcohol III is then treated with a sodium hydride dispersion in an organic solvent (e.g., THF) at about 50° to 70° C., followed by carbon disulfide and a haloalkyl (e.g., iodomethane) at about 20° to 30° C. to form a xanthate of the formula

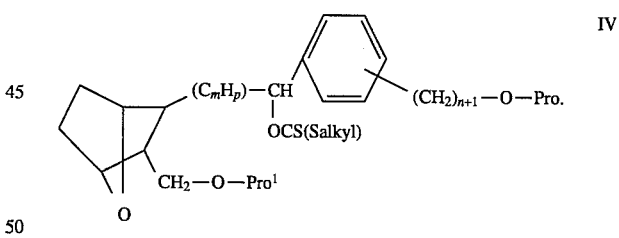

Xanthate IV is heated in toluene at about 100° to 140° C. and undergoes a stereospecific elimination reaction to form an olefin

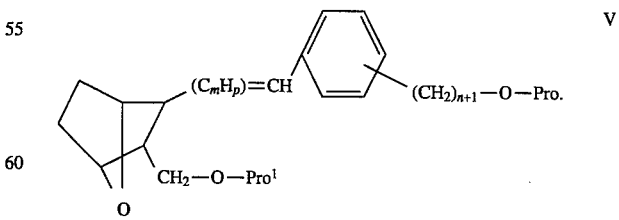

Olefin V is then reacted with Jones reagent (i.e., $CrO_3$ in $H_2SO_4$ in the presence of water, as described in Fieser and Fieser, *Reagents in Organic Synthesis*, 1 (1967), p. 142) in acetone at about −10° to 10° C. and is then reacted with diazomethane to form an olefin-ester

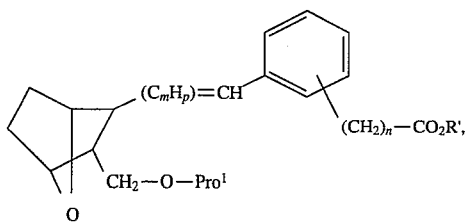

VI wherein R' is alkyl. Compound VI is deprotected by a tetraalkylammonium fluoride (e.g., tetra-n-butylammonium fluoride) in an organic solvent (e.g., THF) at about 20° to 30° C. to form an alcohol

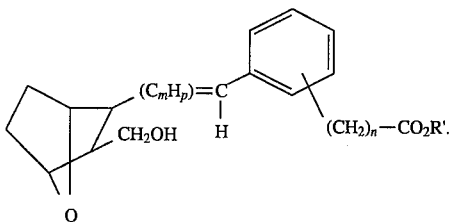

VII

Next, alcohol VII is oxidized by Jones reagent in acetone, to form

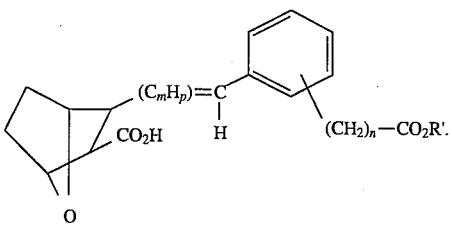

VIII

Acid VIII undergoes a coupling reaction by treatment with amine salt

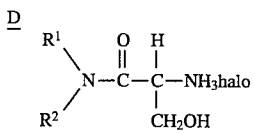

D in an organic solvent such as dimethylformamide (DMF) at about −10° to 10° C. in the presence of dicyclohexylcarbodiimide (DCC) or 1-(3-dimethylaminopropyl)-3-ethylcarbodiimide hydrochloride (WSC) and 1-hydroxybenzotriazole (HOBT) and triethylamine under an inert atmosphere such as argon employing a molar ratio of about 1.2:1 to 1:1 VIII:D to form a hydroxyamide

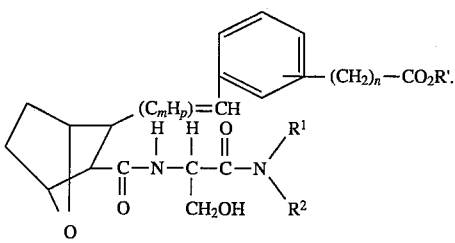

IX

Hydroxyamide IX is then subjected to cyclodehydration in an inert organic solvent (e.g., THF, acetonitrile or methylene chloride) under an inert atmosphere (e.g., argon) with triphenylphosphine (employing a molar ratio of IX:triphenylphosphine of about 0.5:1 to about 1:1) and carbon tetrachloride in the presence of an amine base (e.g., triethylamine or diisopropylethylamine) to form an oxazoline

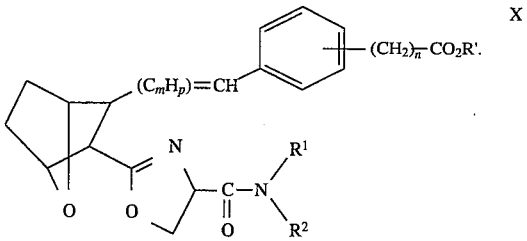

X

Oxazoline X is oxidized by treatment with manganese dioxide or preferably nickel peroxide (see Nakagawa et al., *J. Org. Chem.* 27 (1962), 1597) to form an oxazole

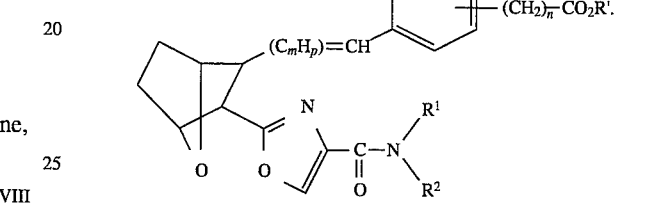

I(B)

Compounds of the invention wherein Y is O and X is O may be prepared as follows.

Bromoanisole E

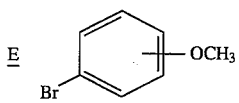

E is metallated (using a procedure similar to that set out above with respect to metal-halogen exchange of B using n-butyllithium in THF) and condensed with hemiacetal C to form the condensed 7-oxabicycloheptane compound

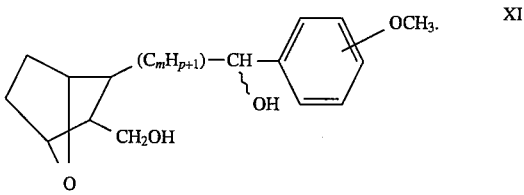

XI

Compound XI is then converted as described for compounds II→III→IV→V to form an olefin XII

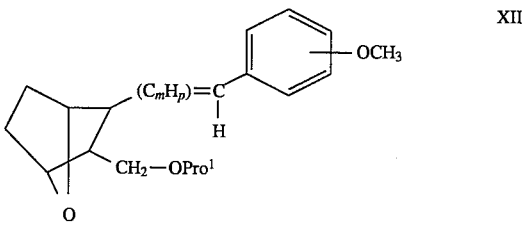

XII

Olefin XII is demethylated (e.g., with lithium iodide in collidene, sodium thiomethoxide in hexamethylphosphoramide) to form phenol XIII

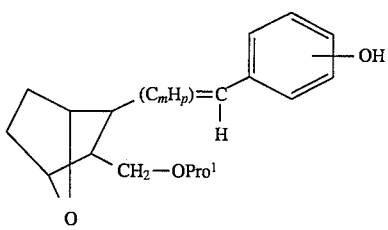
XIII

Phenol XIII is then treated in THF with a molar equivalent of sodium hydride or one to four equivalents of a carbonate base such as potassium carbonate. The resulting phenoxide solution is alkylated by treatment with a haloalkanoic acid ester

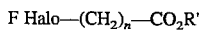

wherein R' is alkyl employing a molar ratio of F:XIII of about 1:1 to about 3:1, in the presence of an inert organic solvent such as THF or DMF or dimethoxyethane, to form ester

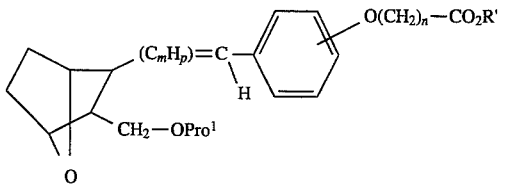
XIV wherein R' is alkyl. Ester XIV is then deprotected by a tetraalkylammonium fluoride (e.g., tetra-n-butyl amonium fluoride) in tetrahydrofuran at about 0° to 30° C. to form alcohol-ester

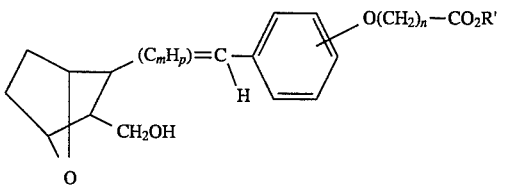
XV

Next, the alcohol-ester XV is subjected to a Jones oxidation at about $-10°$ to 25° C. with Jones reagent to form an acid-ester

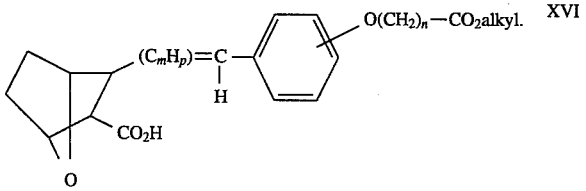
XVI

Acid-ester XVI then undergoes a carbodiimide coupling reaction with an amine hydrochloride

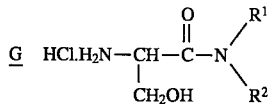

in the presence of triethylamine and DCC or WSC and HOBT under an inert atmosphere (e.g., argon) to form a hydroxyamide

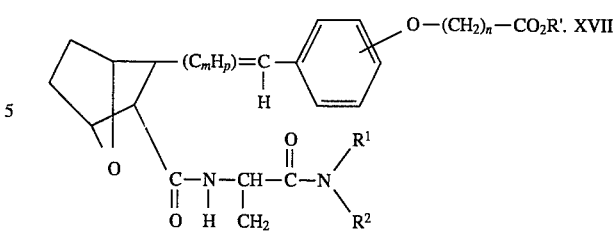
XVII

Hydoxyamide XVII then undergoes cyclodehydration in an inert organic solvent (e.g., THF, acetonitrile, or methylene chloride) under an inert atmosphere (e.g., argon) with triphenylphosphine and carbon tetrachloride in the presence of an amine base (e.g., triethylamine diisopropylethylamine) to form an oxazoline

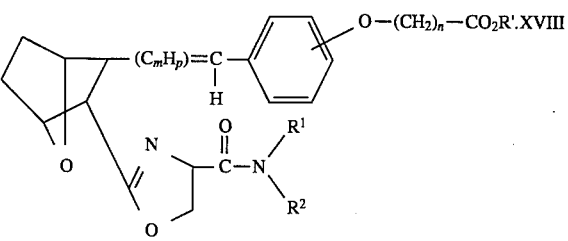
XVIII

Oxazoline XVIII undergoes oxidation with manganese dioxide or nickel peroxide to form an oxazole

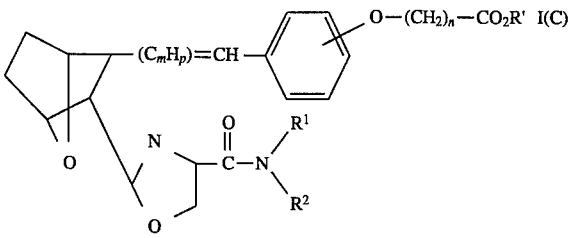
I(C)

Compounds of the invention wherein Y is a single bond or O and X is NH are prepared starting with acids VIII or XVI. Either of acids VIII or XVI undergoes a coupling reaction with an amine

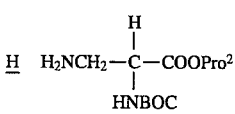

(wherein BOC is t-butyloxycarbonyl and Pro² is protecting group such as benzyl) in the presence of a coupling agent such as WSC and HOBT in methylene chloride for about 12 to 90 hours, employing an acid:amine molar ratio of about 1.2:1 to about 1:1. The resulting amide undergoes a thionation reaction with Lawesson's reagent in the presence of benzene at about 50° to 75° C. for about 1 to 4 hours to form an ester

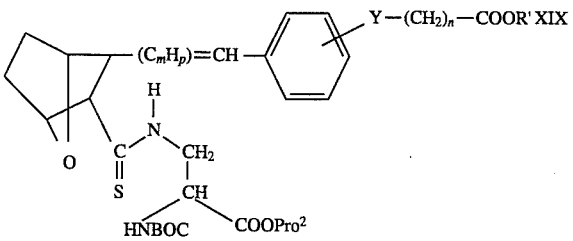
XIX wherein R' is alkyl. The ester XIX is cyclized in an inert solvent (e.g., acetonitrile, methylene chloride or THF) with triphenylphosphine in an ester XIX:triphenylphosphine molar ratio of about 0.8:1 to 1:1 along with carbon tetrachloride in the presence of an amine base (e.g., triethylamine or diisopropylethylamine) to form an imidazoline

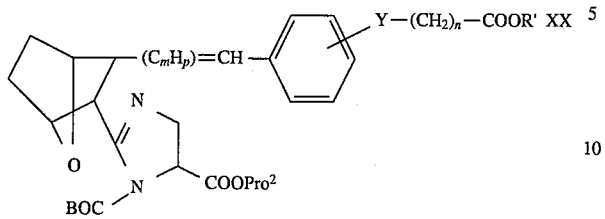

Imidazoline XX is then deprotected to remove the $Pro^2$ protecting group, using conventional procedures to form an acid

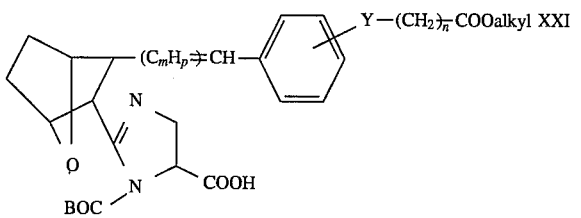

Next, the acid XXI undergoes a coupling reaction with amine

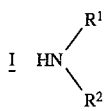

in the presence of an amine base (e.g., pyridine or triethylamine) under an inert atmosphere (e.g., argon) in the presence of a coupling agent such as WSC and HOBT and chloroform, employing a molar ratio of I:XXI of about 0.8:1 to 1.2:1 to form an amide

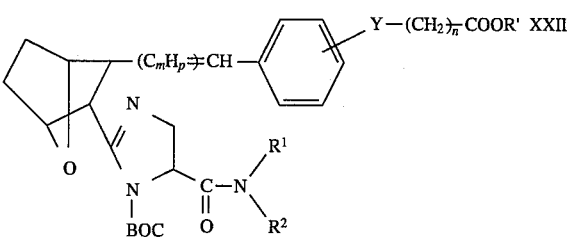

Amide XXII in methylene chloride is then treated with trifluoroacetic acid to remove the BOC group and forms an amide

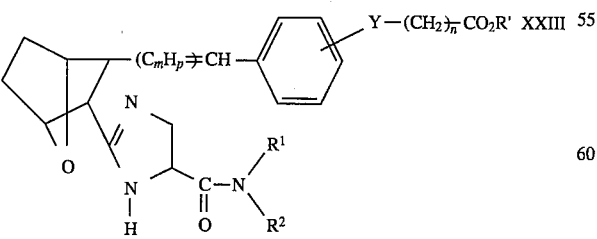

Amide XXIII is oxidized by treatment with an oxidizing agent such as manganese dioxide in the presence of an inert solvent such as chloroform to form ester

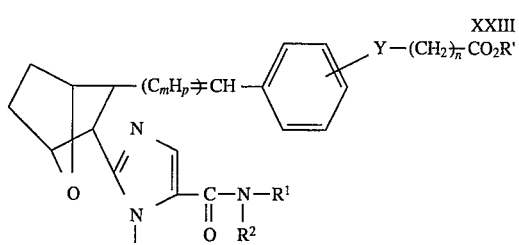

Compounds of the invention wherein n is 0 and Y is a single bond may be prepared starting with a bromobenzyl alcohol

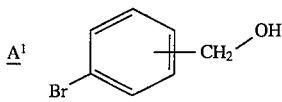

which is treated with a protecting compound (e.g., t-butylchlorodiphenylsilane) in the presence of 4-dimethylaminopyridine and an amine base (e.g., triethylamine) in an inert solvent (e.g., methylene chloride) to form the protected bromobenzyl compound

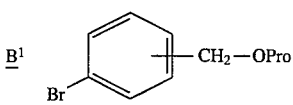

wherein Pro represents a protecting group.

Examples of protecting compounds suitable for use herein with the exclusion of benzyl bromide are as set out hereinbefore in reacting with bromophenalkyl alcohol A.

The protected compound $B^1$ is metallated by treatment with $t{-}C_4H_9Li$ or $n{-}C_4H_9Li$ in the presence of diethyl ether or THF at about $-100°$ to $0°$ C. or is subjected to a Grignard reaction by treatment with magnesium in the presence of an inert organic solvent such as THF or diethyl ether. The so-treated compound $B^1$ is then condensed with compound C in a $C:B^1$ molar ratio of about 1:2 to 1:4 in the presence of an inert organic solvent such as THF at about $-78°$ to $25°$ C. to form a condensed 7-oxabicycloheptane compound

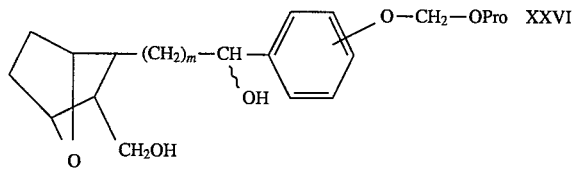

Compound XXIV is then reacted as described above to form

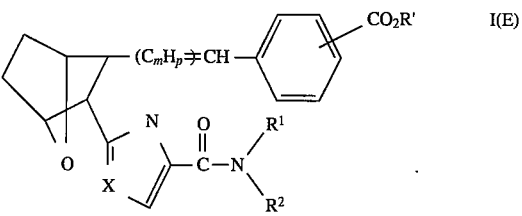

wherein R' is alkyl.

Compounds of formula I wherein Y is —CH═CH— may be prepared starting with alcohol A wherein n is 2, which may be prepared by subjecting the aldehyde

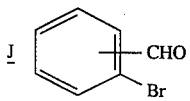

to a Wittig reaction with $(C_6H_5)_3PCHCO_2CH_3$ to form the ester

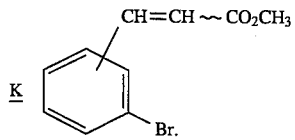

Ester K undergoes a double bond reduction by treatment with hydrogen in the presence of rhodium on alumina catalyst in the presence of methanol to form ester

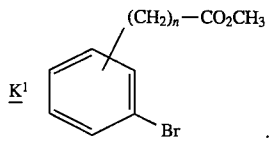

Ester $K^1$ is then reduced by treatment with diisobutylaluminum hydride in the presence of toluene solvent to form alcohol A wherein n is 2.

Alcohol A is used as described previously herein to form alcohol VII wherein n is 2, which is treated with a silane protecting compound as described hereinbefore in the presence of an amine base (e.g., triethylamine) and an inert solvent (e.g., methylene chloride) and N,N-dimethylaminopyridine (DMAP) to form the protected alcohol

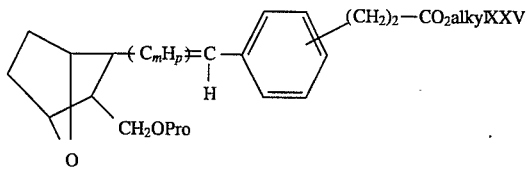

The protected alcohol XXV is then treated with lithium diisopropylamide in the form of a cooled (−78° to 0° C.) mixture of diisopropylamine and t-butyllithium or n-butyllithium under an inert atmosphere (e.g., argon). The resulting mixture is treated with diphenyl diselenide at a temperature of about −78° to 25° C., to form the corresponding selenide

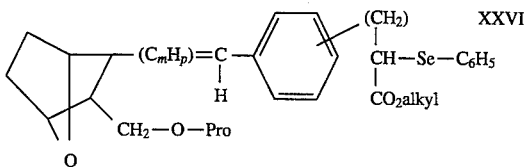

Selenide XXVI in an inert organic solvent (e.g., ethyl acetate and/or methanol ) is treated with an oxidizing agent (e.g., aqueous hydrogen peroxide) to form the cinnamate

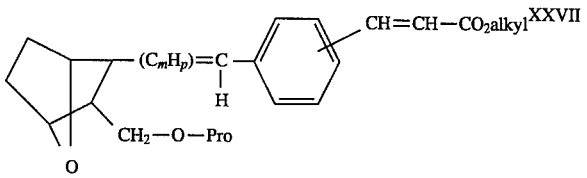

The protecting group is removed from cinnamate XXVII to form the alcohol

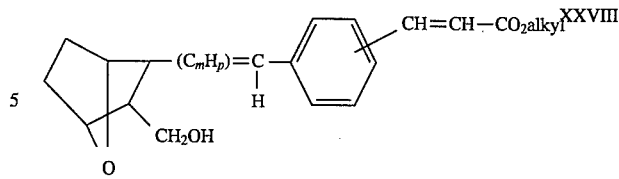

which may then be employed to form compounds of formula I wherein Y is —CH=CH— employing procedures described for treatment of alcoholesters VII and XIV.

Compounds of formula I wherein R is $CO_2R'$ and R' is alkali metal can be prepared from the corresponding esters, such as compounds I(B to E), by treating the ester with bases such as lithium hydroxide or potassium hydroxide. The corresponding acids (wherein R' is hydrogen) are prepared by neutralizing the foregoing alkali metal salts with an acid (e.g., dilute hydrochloric acid or oxalic acid).

Compounds of formula I wherein R is —$CH_2OH$ may be prepared by treating the corresponding esters (wherein R is $CO_2R'$ and R' is alkyl) with a reducing agent such as $LiBH_4$ in the presence of diethyl ether and THF.

Compounds of the invention wherein R is $CONHSO_2R^3$ are prepared by treating the associated acids (wherein R is $CO_2H$) with a sulfonamide

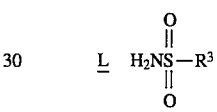

in the presence of a coupling agent (e.g., carbonyldiimidazole or WSC) in the presence of an amine (e.g., DMAP) under an inert atmosphere (e.g., argon).

Compounds wherein R is —$CH_2$—5—tetrazolyl are prepared by reacting the associated ester with, in sequence, (1) a hydride reducing reagent (e.g., lithium borohydride or sodium borohydride), (2) triphenylphosphonium dibromide in an inert solvent such as toluene, (3) an alkali metal cyanide in a polar solvent such as methanol/water, and (4) sodium azide in the presence of ammonium chloride, DMF and lithium chloride at about 100° to 130° C.

Compounds of formula I wherein R is $CONHR^4$ wherein $R^4$ is other than hydrogen may be prepared from the corresponding acid by treatment with WSC in the presence of DMF, HOBT, an organic base (e.g., triethylamine) and an amine

M

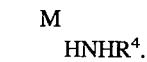

Where $R^4$ in compound I is hydrogen, ammonium chloride is used in place of amine M.

The compounds of this invention have four centers of asymmetry as indicated by the asterisks in formula I. However, it will be apparent that each of the formulae set out above which do not include asterisks still represent all of the possible stereoisomers thereof. All of the various stereoisomeric forms are within the scope of the invention.

The various stereoisomeric forms of the compounds of the invention, namely, cis-exo, cis-endo and all trans forms and stereoisomeric pairs may be prepared with starting materials and procedures in U.S. Pat. No. 4,143,054.

The nucleus in each of the compounds of the invention is depicted as

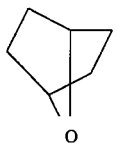

for convenience; the nucleus may also be depicted as

Use and Utility

The compounds of this invention are thromboxane receptor antagonists and as such are useful as inhibitors of thromboxane receptor mediated actions. The term "thromboxane receptor antagonist" includes compounds that are so-called thromboxane $A_2$ receptor antagorists, thromboxane $A_2$ antagonists, thromboxane $A_2$/prostaglandin endoperoxide antagonists, TP-receptor antagonists, or thromboxane antagonists.

The compounds of the invention are also thromboxane synthetase inhibitors and thus are useful as inhibitors of thromboxane production.

The compounds of this invention are useful as inhibitors of platelet function, i.e., for the prevention and treatment of thrombotic vascular occlusive disorders, whether complete or partial, for example, arterial thrombosis, including that of the coronary, cerebral, ophthalmic, hepatic, mesenteric, renal, peripheral arteries or vascular or organ grafts, unstable angina, transient ischemic attacks, or intermittent claudication. They may be useful to prevent thrombosis following vascular injury produced in the course of diagnostic or therapeutic procedures such as endarterectomy or angiography. The compounds may be useful in the treatment or prevention of disorders characterized by platelet consumption and/or activation, including, platelet activation, dysfunction, and/or loss during extracorporeal circulation, the use of radiographic contrast agents, thrombotic thrombocytopenia purpura, disseminated intravascular coagulation, purpura fulminans, hemolytic transfusion reaction, or hemolytic uremic syndrome, systemic lupus, cyclosporine-induced renal toxicity, pulmonary hypertension, side effects from dialysis, or abdominal aortic aneurism repair. The compounds may be used in the treatment of venous thrombosis or embolism, including pulmonary embolism, deep venous thrombosis, hepatic vein thrombosis, and renal vein thrombosis.

The compounds of this invention are useful as inhibitors of arterial or venous vasoconstriction. Accordingly, they may be useful to prevent vasoconstriction associated with unstable angina, chronic stable angina, and variant, or Prinzmetal's angina, Raynaud's syndrome, migraine headache, vasospasm of the coronary, cerebral, ophthalmic, hepatic, mesenteric, renal, peripheral arteries or vascular grafts, vascular injury such as that associated with surgery or trauma. Hypertension of pregnancy, the hepato-renal syndrome, and pulmonary hypertension are additional examples of vasoconstrictive disorders treatable by the compounds of this invention.

The compounds of this invention are useful as inhibitors of bronchoconstriction, i.e., airway hyperresponsiveness, allergic bronchospasm, asthma, and bronchoconstrictive responses to environmental, infectious, noxious or mechanical stimuli.

The compounds of this invention are useful as inhibitors of ischemic and reperfusion injury to various tissues, including, myocardium, skin, brain, bowel, or kidney, alone or in combination with other agents intended to restore blood flow. For example, these compounds may be useful for improving postischemic myocardial function and decreasing myocardial infarct size. Ischemia caused by reduced blood flow during diagnostic or therapeutic procedures may benefit by treatment with these compounds, for example, they reduce the myocardial stunning observed after bypass surgery. In addition, they may be useful for reducing the tissue injury caused by a stroke.

The compounds of this invention may be useful in the prevention or treatment of other conditions including burns, diabetic retinopathy, tumor metastases and tardive dyskinesia. The compounds may be useful in potentiating diuretic-induced diuresis.

In addition, the thromboxane receptor antagonists of the invention may be used with a thrombolytic agent such as t-PA, streptokinase, urokinase, prourokinase or anisoylated plasminogen-streptokinase activator complex (APSAC) within 6 hours of a myocardial infarction. In such case, the thrombolytic agent may be used in amounts conventionally employed, for example, as disclosed in the Physicians' Desk Reference for reducing post-ischemic myocardial injury.

The compounds of the invention can be administered orally or parenterally to various mammalian species known to be subject to such maladies, e.g., humans, cats, dogs and the like in an effective amount within the dosage range of about 0.1 to about 100 mg/kg, preferably about 0.2 to about 50 mg/kg and more preferably about 0.5 to about 25 mg/kg (or from about 1 to about 2500 mg, preferably from about 5 to about 2000 mg) on a regimen in single or 2 to 4 divided daily doses.

The active substance can be utilized in a composition such as tablet, capsule, solution or suspension containing about 5 to about 500 mg per unit of dosage of a compound or mixture of compounds of formula I or in topical form for wound healing (0.01 to 5% by weight compound of formula I, 1 to 5 treatments per day). They may be compounded in conventional matter with a physiologically acceptable vehicle or carrier, excipient, binder, preservative, stabilizer, flavor, etc., or with a topical carrier such as Plastibase (mineral oil gelled with polyethylene) as called for by accepted pharmaceutical practice. Also as indicated in the discussion above, certain members additionally serve as intermediates for other members of the group.

The compounds of the invention may also be administered topically to treat peripheral vascular diseases and as such may be formulated as a cream or ointment.

PREFERRED EMBODIMENTS

The following Examples represent preferred embodiments of the present invention. Unless otherwise indicated, all temperatures are expressed in degrees Celsius.

EXAMPLE 1

[1S-[1α, 2Z, 3α, 4α]]-2-[[3-[4-[[4 -Cyclohexylbutyl)-amino]carbonyl]-2-oxazolyl]-7-oxabicyclo[2.2.1] -hept-2-ylidene]methyl]benzenepropanoic acid

A. 3-(2-Bromophenyl)-2-propenoic acid, methyl ester

To a stirred solution of 161.2 g (871 mmol) of 2-bromobenzaldehyde in 700 mL of dry THF (distilled from potassium/benzophenone) at room temperature under argon, was added 298.4 g (892 mmol, 1.024 equiv) of methyl(triphenylphosphoranylidene)acetate (Aldrich) over 1 hour in 20 g portions. Reaction was mildly exothermic and the mixture became homogeneous. The resulting solution was stirred for 18 hours during which some precipitate formed. Addition of 200 mL hexane caused further precipitation. Filtration was followed by evaporation. The residue was slurried with a large volume of hexane (more precipitation) and refrigerated overnight. This was filtered, and the filtrate was passed through a plug of silica gel (approximately 1 kg), eluting with 10% ethyl acetate (EtOAc) in hexane. The eluant was concentrated in vacuo to give 201.5 g of a colorless oil. This oil was pure title compound as a 4:1 mixture of double bond isomers (trans predominating). The yield of title compound was 96%.

B. 2-Bromobenzenepropanoic acid, methyl ester

A mixture of 201.5 g (836 mmol) of Part A acrylate and 8.4 g of 5% rhodium on alumina catalyst (MCB) in 1.0 L of methanol was stirred at room temperature under an atmosphere of hydrogen (balloon) for over 8 hours. $^1$H NMR analysis of an aliquot showed about a 1:1 mixture of title compound and trans Part A compound with no cis Part A compound. The mixture was diluted with 500 mL additional methanol (MeOH) and 12.6 g more catalyst was added. After hydrogenation overnight, the reaction was complete. The reaction mixture was passed through Celite and a Millipore/Fluropore membrane filter (0.5 μm FH) with a prefilter pad, and the filtrate was concentrated in vacuo to obtain two immiscible oils. One of the oils was water-soluble and gave a highly acid aqueous solution. Solid $NaHCO_3$ and $Na_2SO_4$ were carefully added (gas was evolved). The mixture was diluted with $CH_2Cl_2$, filtered, and evaporated (and re-evaporated with $CH_2Cl_2$ to drive off methanol) to obtain 196.9 g of clear oil. This oil was 95% pure title compound with 5% of the bromo title compound. The corrected yield of the title compound was 92% (187.1 g).

C. 2-Bromobenzenepropanol

To a stirring solution of 196.9 g (95% pure, 187.1 g, 770 mmol) of Part B compound in 770 mL of toluene under argon cooled to 0° (ice bath), was added over 45 minutes 830 mL of 1.0 M diisobutylaluminum hydride (DIBAL-H) in toluene solution (830 mmol). The reaction was not very exothermic. After the mixture was stirred for 1 hour, TLC indicated approximately half of the starting material remained. Next, 580 mL of 1.5 M DIBAL-H in toluene solution (870 mmol) was added slowly. The ice bath was removed and stirring was continued for 2 hours. The mixture was then poured slowly into 1.2 L of 6 M aqueous HCl stirring in an ice bath. This quench was exothermic and gas was evolved. After the mixture was recooled to 0°, the layers were separated, and the organic layer was washed with 1M aqueous HCl and brine. It was then dried over $Na_2SO_4$ and $MgSO_4$ and evaporated (and re-evaporated with $CH_2Cl_2$ to drive off toluene) to obtain 173.0 g of a clear, colorless oil. This oil was 95% pure title compound with 5% of the part B title compound. The corrected yield of title compound was 99% (164.3 g).

D. [3-(2-Bromophenyl)propoxy]dimethyl-(1,1,2-trimethylpropyl)silane

To a stirring solution of 173.0 g (95% pure, 164.3 g, 764 mmol) of Part C compound and 57.8 g of imidazole (850 mmol) in 1.0 L of $CHCl_3$ at room temperature was added slowly 136.6 g (764 mmol) of thexyldimethylchlorosilane. The reaction was mildly exothermic and a precipitate formed. After stirring overnight, $^1$H NMR analysis of an aliquot showed a trace of Part C compound remaining. Additional thexyldimethylchlorosilane (6.8 g, 38 mmol, 0.05 equiv) was added. After 2 days, the mixture was evaporated. The residue was diluted with hexane and filtered. The filtrate was evaporated and distilled (150°–180° at 1.2 torr) to obtain 262.8 g of slightly cloudy, colorless oil. This oil was 94% pure title compound with 5% of the part B title compound. The corrected yield of title compound was 91% (247.0 g).

E. Bromo[2-[3-[[dimethyl(1,1,2-trimethylpropyl)silyl]oxy]propyl]phenyl]magnesium A 2-L oven-dried flask containing a magnetic stir-bar was charged with 19.0 g of hammer-crushed Mg turnings (782 mmol) and placed under an argon atmosphere. After 440 mL dry THF (distilled from potassium/benzophenone) was added, the Mg was activated at room temperature by introduction of a crystal of iodine and 2 mL of 1,2-dibromoethane (gas was evolved). This was followed by addition of 207.4 g (94% pure, 195.0 g, 546 mmol) of Part D compound in a single portion. The reaction mixture briefly turned colorless, then amber. The exothermic reaction brought the mixture to reflux. Additional dry THF (120 mL) was introduced to ensure product solubility on eventual cooling. Although the reaction was not violently exothermic, foaming made it necessary to cool the mixture with a water bath. The water bath was used intermittently until the exotherm subsided. The mixture was then heated to a gentle reflux for 1 hour and cooled to room temperature. No precipitate formed. The mixture consisted of a brown, clear solution of title compound and some unreacted Mg.

F. (1α, 2α,3α,4ζ)-α-[2-[3-[[Dimethyl-(1,1,2-trimethylpropyl)silyl]oxy]propyl]-phenyl]-7-oxabicyclo[2.2.1]heptane-2,3-dimethanol A 5-L flask containing a magnetic stir-bar was charged with 63.1 g of [3aR-(3aα, 4β, 7β, 7aα)]-octahydro-4,7-epoxyisobenzofuran-1-ol (405 mmol) and placed under an argon atmosphere. After 400 mL dry THF (distilled from potassium/benzophenone) was added, [3aR-(3aα, 4β, 7β, 7aα)]-octahydro-4,7-epoxyisobenzofuran-1-ol was dissolved by stirring. The resulting solution was cooled to 0°, and by syringe over 30 minutes, 192 mL of 2.0 M $C_2H_5MgBr$ (prewarmed to 30° to ensure homogeneity, 385 mmol, 0.95 equiv) was added. Gas was evolved. After the addition was complete, stirring at 0° C. was continued for 1 hour. The solution of previously prepared Part E magnesium compound (546 mmol, 1.35 equiv theoretical) was introduced by cannula over 1 hour. The temperature was maintained at 0° C. during the addition and for several hours afterward. A small amount of precipitate formed. The mixture was warmed to room temperature, and 50 mL dry THF was added. Some precipitate remained. This mixture was stirred for 6 days before 290 mL of a saturated, aqueous solution of $NH_4Cl$ (83 g) was slowly added. The quench was slightly exothermic, the mixture warming itself to about 40° C. The mixture was stirred for 2 hours, and the inorganics formed a white paste. To the mixture was added 1.0 L of $CH_2Cl_2$. The organic supernatant was decanted from the paste. The paste was then stirred with 500 mL $CH_2Cl_2$. The organic layer was decanted, and this procedure was repeated. The combined organic layers were dried over 115 g $Na_2SO_4$ (total volume 3.5 L), and concentrated in vacuo. To drive off THF the residue was re-concentrated after addition of 200 mL $CH_2Cl_2$. This yielded 230 g of an oil. The oil was then quickly dissolved in 2.0 L hexane. Crystallization began in minutes. The mixture was refrigerated with periodic agitation for 5 days. The crystals which formed were filtered (cold) and washed with two 500-mL portions of refrigerated hexane. After exposure to vacuum, 145.9 g of crystals (mp 99.5°–100.5° C.) were obtained. The crystals, pure and a single diastereomer of Part F compound, represented an 83% yield.

The mother liquors were evaporated, redissolved in 200 mL hexane, and placed in the freezer for 30 days. A second crop of crystals (8.7 g, pure, single diastereomer of Part F compound, 5% additional yield) was collected as above. The mother liquors from this preparation were concentrated in vacuo to give an oil. The crude oil was purified by flash chromatography (Merck silica, 25×10 cm, 1:4 ethyl acetate/hexane then ethyl acetate) to afford 12.2 g (28.1 mmol, 7%) of diol R and S isomers as a yellow oil. 270 MHz $^1$H NMR indicated the diastereomeric ratio of about 1:1.

[1S-(1α, 2α(R*), 3α, 4α)]-3-[[[(1,1-Dimethylethyl)diphenylsilyl]oxy]methyl-α-[2-[2 -[[dimethyl(1,1,2-trimethylpropyl)silyl]-oxy]ethyl]phenyl]-7-oxabicyclo[2.2.1]-heptane-2-methanol; and [1S-(1α, 2α(S*), 3α, 4α)]-3-[[[(1,1-Dimethylethyl)diphenylsilyl]-oxy]methyl-α-[2-[2 -[[dimethyl(1,1,2-trimethylpropyl)silyl]-oxy]ethyl]phenyl]-7-oxabicyclo[2.2.1] -heptane-2-methanol To a solution of 11.0 g (25.3 mmol) of the diastereomeric mixture from part F in 100 mL of dry methylene chloride (distilled from phosphorous pentoxide) was added at room temperature 4.5 mL (32 mmol) of reagent triethylamine, 6.97 g (25.3 mmol) of t-butylchlorodiphenylsilane and then 150 mg (1.23 mmol) of 4-dimethylaminopyridine. The reaction was stirred for 18 hours, then diluted with 200 mL of hexane and cooled in a refrigerator. The amine salt that precipitated was removed by filtration, and the filtrate was concentrated in vacuo to give an oil. The crude oil was purified by flash chromatography (Merck silica gel, 20×10 cm, 1:15 and then 1:4 ethyl acetate/hexane) to elute first 8.20 g (12.2 mmol) of the S isomer as a colorless oil, then 2.60 g (3.87 mmol, 15%) of the R isomer as a colorless oil.

H. [1S-(1α, 2α(S*), 3α, 4α)]-3-[[[(1,1-Dimethylethyl)diphenylsilyl]oxy]methyl] -α-[2-[2-[[dimethyl(1,1,2-trimethylpropyl)silyl]-oxy]ethyl]phenyl]-7-oxabicyclo[2.2.1] -heptane-2-methanol, (methylthio)thiocarbonate ester To a solution of 5.17 g (7.69 mmol) of the S isomer from part G in 50 mL of dry THF (distilled from sodium/benzophenone) was added in several portions a total of 340 mg (60% in oil, 8.5 mmol, Aldrich) of sodium hydride dispersion then a small drop of water. The reaction was heated to 60° until gas evolution ceased, which took about 30 minutes. The reaction was cooled to room temperature and 1.0 mL (17 mmol, Mallinckrodt) of carbon disulfide was added in one portion. After 20 hours, 1.0 mL (16.0 mmol, Mallinckrodt) of iodomethane was added dropwise. The reaction mixture was stirred for 15 minutes, quenched by slow addition of 5 mL of water, and partitioned between 50 mL of ethyl acetate and 150 mL of water. The organic layer was separated and the aqueous layer was extracted with an additional 50 mL of ethyl acetate. The organic extracts were combined, dried (magnesium sulfate) and concentrated in vacuo to give a yellow oil. The crude oil was purified by flash chromatography (Merck silica, 20×5.0 cm, 1:20 ethyl acetate/hexane) to afford 4.00 g (5.25 mmol, 68%) of xanthate H as a yellow oil. In addition 1.29 g (1.92 mmol, 25%) of starting S-isomer alcohol G was recovered.

I. [1S-(1α, 2α(Z), 3α, 4α)]-3-[[[(1,1-Dimethylethyl)diphenylsilyl] -oxy]methyl] -2-[ [2- [3 -[ [dimethyl(1,1,2-trimethylpropyl)silyl] -oxy]propyl] phenyl] methylidene]-7-oxabicyclo-[2.2.1]heptane A solution of 3.98 g (5.22 mmol) of xanthate H in 50 mL of toluene (Burdick and Jackson) was placed into an oil bath heated at 120° for 2.5 hours. The resulting solution was cooled and then concentrated in vacuo to give 3.41 g (5.21 mmol, 100%) of olefin I as a yellow oil.

J. [1S-(1α, 2α(Z), 3α, 4α)]-2-[[3-[[(1,1 -Dimethylethyl)diphenylsilyl]oxy]methyl]-7-oxabicyclo[2.2.1]hept-2-ylidene]methyl]-benzenepropanoic acid, methyl ester To a solution of (7.57 mmol) of the part I olefin in 50 mL of reagent acetone cooled in an ice-bath was added dropwise over 10 minutes 10 mL (2.6 mL in $Cr^{+6}$) of Jones reagent (prepared as described in Fieser and Fieser, *Reagents for Organic Synthesis*, Vol. 1). The reaction mixture was stirred for 2.5 hours, quenched by addition of about 5 mL of isopropanol, and stirred for 20 minutes. The resulting green slurry was filtered through a pad of Celite. The salts were rinsed first with additional acetone, then with methylene chloride. The filtrate was concentrated in vacuo and the residue partitioned between 50 mL of ethyl acetate and 50 mL of water. The organic layer was separated, dried (magnesium sulfate) and then treated with excess ethereal diazomethane at 0° C. After 10 minutes, glacial acetic acid was added dropwise to quench the excess diazomethane and the solution was concentrated in vacuo to give an oil. The crude material was purified by flash chromatography (Merck silica, 15×5.0 cm, 1:19 ethyl acetate/hexane) to give ester J contaminated with volatile silyl byproducts. This material was heated to 60° under oil pump vacuum (0.5 mm) to remove volatiles and afforded a residue of 2.40 g (4.43 mmol, 59%) of pure ester J as a colorless oil.

K. [1S-(1α,2α(Z), 3α, 4α)]-2-[[3 -(Hydroxymethyl)-7-oxabicyclo[2.2.1]hept-2-ylidene]-methyl]benzenepropanoic acid, methyl ester To a solution of 2.38 g (4.39 mmol) of ester J in 10 mL of dry THF (distilled from sodium/benzophenone) was added dropwise 5.0 mL (1.0 M in THF, 5.0 mmol, Aldrich) of tetra-n-butylammonium fluoride solution at room temperature. The resulting solution was stirred for 2 hours, added to 75 mL of water, and extracted with two 50-mL portions of ethyl acetate. The organic layers were combined, dried (magnesium sulfate) and concentrated in vacuo to give an oil. The crude oil was purified by flash chromatography (Merck silica, 15×5.0 cm, 3:1 ethyl acetate/hexane) to give 1.16 g (3.84 mmol, 87%) of alcohol K as a colorless oil.

L. N-(4-Cyclohexylbutyl)-L-serinamide, monohydrochloride

To a solution of 14.3 g of 4-cyclohexylbutylamine hydrochloride (74.7 mmol), 16.1 g BOC-(L)-serine (78.4 mmol, 1.05 equiv), 10.1 g HOBT hydrate (74.7 mmol, 1.00 equiv), and 7.9 g N-methylmorpholine (78.4 mmol, 1.05 equiv) in 200 mL DMF stirring under argon at 0°, was added 15.0 g WSC (78.4 mmol, 1.05 equiv) in a single portion. All of the WSC dissolved. The reaction mixture was allowed to slowly warm to room temperature overnight, and a precipitate formed. The mixture was rotoevaporated (60° bath) to 90 g of oil plus solid. This oil and solid mixture was diluted with 400 mL EtOAc and washed with 200 mL 0.3 M aqueous HCl twice (all solids dissolved at this point), then 200 mL 1.0 M aqueous $NaHCO_3$ twice. To the organic layer was added 500 mL toluene, and this was dried over $Na_2SO_4$ and evaporated. After coevaporation with toluene, 28.4 g of a thick solidifying oil was obtained. This material was dissolved in 150 mL $CH_2Cl_2$ and, while stirring at room temperature under argon, 100 mL trifluoroacetic acid was added (gas was evolved). After 4 hours, the solvent was evaporated. After coevaporation with $CHCl_3$, the crude product was flash chromatographed (1.0 kg silica gel, 10% (10% concentrated aqueous NH₃ in methanol in CH₂Cl₂) to obtain 13.4 g of 95% pure compound L as a white solid. The correct yield was 70% (12.7 g) overall from 4-cyclohexylbutylamine hydrochloride.

M. [1S-(1α, 2α(Z), 3α(R*), 4α)]-2-[[3-[[[2-[(4 -Cyclohexylbutyl)amino]-1-(hydroxymethyl)-2 -oxoethyl]amino]carbonyl]-7-oxabicyclo-[2.2.1]hept-2-ylidene]methyl]benzenepropanoic acid, methyl ester To a solution of 1.15 g (3.81 mmol) of alcohol K in 12 mL of reagent acetone cooled in an ice-bath was added 2.0 mL (2.6 M in Or⁺⁶) of Jones reagent over several minutes. The reaction was stirred for 1 hour, and an additional 2.0 mL of Jones reagent was added. After 1 hour the reaction was quenched by addition of 2 mL of isopropanol, stirred for 20 minutes, and filtered through a pad of Celite. The filtrate was added to 75 mL of 1 M aqueous hydrochloric acid solution and extracted with two 30-mL portions of ethyl acetate. The organic extracts were combined, washed with 25 mL of brine, dried (magnesium sulfate) and concentrated in vacuo to give the crude acid as an oil. To a solution of the crude acid in 20 mL of sieve-dried DMF cooled in an ice-bath were added 1.06 g (3.81 mmol) of amine hydrochloride L, 566 mg (4.19 mmol) of 1-hydroxybenzotriazole hydrate, and 0.60 mL (4.3 mmol, distilled from calcium hydride) of triethylamine. The mixture was stirred for several minutes, and 804 mg (4.19 mmol) of WSC was added. The reaction was stirred at 0° for 3 hours, then at room temperature for 16 hours, followed by partitioning between 100 mL of 1 M aqueous hydrochloric acid and 40 mL of ethyl acetate. The organic layer was separated and the aqueous layer extracted with an additional 40 mL of ethyl acetate. The organic extracts were combined, dried (magnesium sulfate) and concentrated in vacuo to give an oil. The crude material was purified by flash chromatography (Merck silica, 12×5.0 cm, ethyl acetate then 1:50 methanol/ethyl acetate) to afford 1.19 g (2.21 mmol, 58%) of compound M as a pale yellow solid, melting point 128°–131°.

N. [1S-(1α, 2α(Z), 3α, 4α)]-2-[[3-[4-[[(4 -Cyclohexylbutyl)amino]carbonyl]-4,5-dihydro-2 -oxazolyl] -7-oxabicyclo[2.2.1]hept-2 -ylidene]methyl]benzenepropanoic acid, methyl ester A mixture of 900 mg (1.67 mmol) of compound M in 16 mL of 3:1 acetonitrile/methylene chloride was warmed until homogeneous, then cooled to room temperature. To the resulting solution was added 875 mg (3.34 mmol, Aldrich) of triphenylphosphine and 870 µl (5.0 mmol, Aldrich) of diisopropylethylamine. After 5 minutes, 325 µl (3.3 mmol) of carbon tetrachloride was added. The reaction mixture was stirred for 18 hours, then partitioned between 50 mL of ethyl acetate and 75 mL of saturated aqueous sodium bicarbonate solution. The organic layer was separated, washed with 25 mL of brine, dried (sodium sulfate) and concentrated in vacuo to give a dark oily solid. The crude material was purified by flash chromatography (Merck silica, 15×5.0 cm, 2:3 acetone/hexane) to give 750 mg (1.44 mmol, 86%) of oxazoline N as a yellow oil.

O. [1S-(1α, 2α(Z), 3α, 4α)]-2-[ [3-[4-[ [(4 -Cyclohexylbutyl)amino]carbonyl]-2-oxazolyl]-7 -oxabicyclo[2.2.1]hept-2-ylidene]methyl]-benzenepropanoic acid, methyl ester To a solution of 720 mg (1.38 mmol) of oxazoline N in 20 mL of dry methylene chloride (distilled from phosphorous pentoxide) cooled in an ambient water bath was added 1.5 g of nickel peroxide catalyst (prepared as described by Nakagawa et al., *J. Org. Chem.*, 27, (1962) 1597). Two successive additions of 1.5 g and 0.5 g of catalyst were made at 30-minute intervals until the starting material was consumed (determined by TLC), then 50 mL of ethyl acetate and 50 mL of 3 M aqueous sodium bisulfite solution were added. The mixture was stirred rapidly for 30 minutes, during which time the nickel precipitate dissolved. The resulting emulsion was poured into 50 mL of 1 M aqueous sodium citrate solution. The organic layer was separated, and the aqueous layer was extracted with an additional 25 mL of ethyl acetate. The organic extracts were combined, dried (magnesium sulfate) and concentrated in vacuo to give a yellow solid. The crude material was purified by flash chromatography (Merck silica, 15×3.0 cm, 2:1 ethyl acetate/hexane) to afford 365 mg (0.70 mmol, 51%) of oxazole ester O as a white solid, melting point 118°–119°.

P. [1S-[1α, 2Z, 3α, 4α]]-2-[[3-[4-[[(4 -Cyclohexylbutyl)amino]carbonyl]-2-oxazolyl]-7 -oxabicyclo[2.2.1]hept-2-ylidene]methyl]-benzenepropanoic acid To a solution of 340 mg (0.65 mmol) of oxazole ester O in 3 mL of 2:1 THF/water was added 55 mg (1.3 mmol) of lithium hydroxide monohydrate at room temperature. The reaction mixture was stirred rapidly for 3 hours, acidified with 3 mL of aqueous hydrochloric acid, and then partitioned between 20 mL of water and 20 mL of ethyl acetate. The organic layer was separated, dried (magnesium sulfate) and concentrated in vacuo to give an oil. TLC and ¹H NMR showed the oil as about a 3:1 mixture of exo and endo oxazole isomers. The crude material was purified by flash chromatography (Merck silica, 15×3.0 cm, 1:19 methanol/methylene chloride) to give a solid which was recrystallized (ethyl acetate) twice to give 148 mg (0.29 mmol, 45%) of the title compound, melting point 136°–138°. IR(KBr): 3426, 2924, 1711, 1694, 1642, 1605, 1526 cm⁻¹.

TLC: $R_f$ (silica gel, 1:19 methanol/methylene chloride)= 0.29, ammonium molybdate/ceric sulfate and UV.

TLC Quantitation: (silica gel, 1:19 methanol/methylene chloride, UV at 245 nM) indicates the exo/endo mixture was 125:1.

Analysis calculated for $C_{30}H_{38}N_2O_5$: C,71.12; H,7.56; N,5.53

Found: C,70.90; H,7.26; N,5.41.

EXAMPLE 2

1S-[1α, 2Z, 3α, 4α]]-2-[[3-[4-[[ -(4-Cyclohexylbutyl)amino]carbonyl] -2-oxazolyl] -7 -oxabicyclo[2.2.1]hept-2-ylidene]methyl]benzenepropanoic acid The fractions containing the slower moving isomer from the flash chromatography of the crude hydrolysis product of 340 mg (0.65 mmol) from Example 1, part M were combined and concentrated in vacuo to give a solid. The solid was recrystallized (ethyl acetate/hexane) to afford 30 mg (0,063 mmol, 10%) of Example 2 as a white solid, melting point 142°–144°.

TLC: $R_f$ (silica gel, 1:19 methanol/methylene chloride)= 0.21, ammonium molybdate/ceric sulfate and UV.

TLC Quantitation: (silica gel; 1:19 methanol/methylene chloride, I/V at 245 nM) indicates the endo/exo mixture as 96:4.

Analysis calculated for $C_{30}H_{38}N_2O_5$: C,71.12; H,7.56; N,5.53

Found: C,71.21; H,7.64; N,5.35

What is claimed is:
1. A compound having the formula

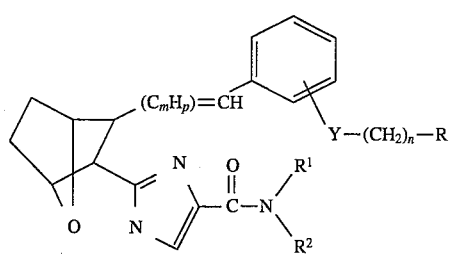

including all stereoisomers and pharmaceutically acceptable salts thereof, wherein:

$C_mH_p$ is an alkylene chain wherein m is 0, 1, 2, or 3 and p=(2×m)−1, except that when m is 0, p is also 0;

n is 0, 1, 2 or 3;

R is $CO_2R'$, $CH_2OH$, $CONHSO_2R^3$, $CONHR^4$, or $-CH_2$-5-tetrazolyl;

R' is hydrogen, alkyl, or alkali metal;

X is O or NH;

Y is —O—, a single bond or vinylene, except that Y cannot be —O— when n is 0;

$R^1$ is hydrogen, alkyl, alkenyl, alkynyl, aralkyl, aryl, cycloalkyl, cycloalkylalkyl, cycloheteroalkyl, cycloheteroalkylalkyl, heteroaryl, heteroarylalkyl, $-(CH_2)_t-C(O)-N(H)-R_a$ or $-(CH_2)_t-N(H)-C(O)-R_a$ wherein t is 1 to 12 and $R_a$ is alkyl, aryl, cycloalkyl, or cycloalkylalkyl), each of $R^1$ being unsubstituted or optionally substituted with alkyl, aryl, cycloalkyl, or cycloalkylalkyl;

$R^2$ is hydrogen, alkyl, aryl, or aralkyl; or $R^1$ and $R^2$, together with the nitrogen atom to which they are linked, form a 5- to 8-membered ring;

$R^3$ is alkyl, aryl or aralkyl;

$R^4$ is hydrogen, alkyl, aryl or aralkyl;

"alkyl" refers to groups of up to 12 carbon atoms;

"cycloalkyl" refers to cyclic groups of 3 to 12 carbon atoms;

"aryl" refers to monocyclic or bicyclic aromatic groups containing from 6 to 10 carbon atoms in the ring portion;

"cycloheteroalkyl" refers to 5-, 6- or 7-membered saturated rings that include one or two heteroatoms selected from nitrogen, oxygen and sulfur, which are linked through a carbon atom either beta or gamma to a heteroatom;

"heteroaryl" refers to 5-, or 6-membered aromatic rings that include one or two heteroatoms selected from nitrogen, oxygen, and sulfur, which are not attached directly by a heteroatom to the "N" of the $-NR^1R^2$ group;

"cycloheteroalkylakyl" refers to 5-, 6- or 7-membered saturated rings that include one or two heteroatoms selected from nitrogen, oxygen, and sulfur, and are linked to the "N" of the $-NR^1R^2$ group through a $(CH_2)_x$ chain wherein x is 1 to 12;

"heteroaryalkyl" refers to 5-, 6- or 7-membered aromatic rings that include one to four nitrogen and/or one or two oxygen or sulfur atoms and is linked to the "N" of the $-NR^1R^2$ group through a $(CH_2)_x$ chain wherein x is one to 12; and "5- to 8-membered ring 11 refers to a cycloheteroalkyl or heteroaryl group wherein the "N" of the $-NR^1R^2$ group is the only heteroatom.

2. The compound of claim 1 having the formula

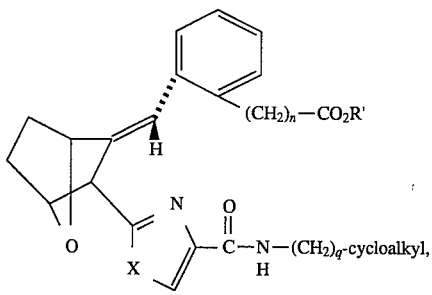

wherein:

q is an integer from 1 to 7; and

R' is hydrogen, alkyl, or alkali metal.

3. The compound of claim 1, wherein X is oxygen.

4. The compound of claim 2, wherein X is oxygen.

5. The compound of claim 2, wherein q is 4.

6. The compound of claim 1, wherein n is 2.

7. The compound of claim 2, wherein n is 2.

8. The compound of claim 2, wherein the cycloalkyl group is cyclohexane.

9. A compound having the formula

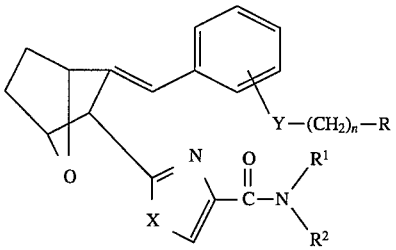

including all stereoisomers and pharmaceutically acceptable salts thereof, wherein:

n is 0, 1, 2 or 3;

R is $CO_2R'$, $CH_2OH$, $CONHSO_2R^3$, $CONHR^4$, or $-CH_2-5-$tetrazolyl;

R' is hydrogen, alkyl, or alkali metal;

X is O or NH;

Y is —O—, a single bond or vinylene, except that Y cannot be —O— when n is 0;

$R^1$ is hydrogen, alkyl, alkenyl, alkynyl, aralkyl, aryl, cycloalkyl, cycloalkylalkyl, cycloheteroalkyl, cycloheteroalkylalkyl, heteroaryl, heteroarylalkyl, $-(CH_2)_t-C(O)-N(H)-R_a$ or $-(CH_2)_t-N(H)-C(O)-R_a$ (wherein t is 1 to 12 and $R_a$ is alkyl, aryl, cycloalkyl, or cycloalkylalkyl), each of $R^1$ being unsubstituted or optionally substituted with alkyl, aryl, cycloalkyl, or cycloalkylalkyl;

$R^2$ is hydrogen, alkyl, aryl, or aralkyl; or $R^1$ and $R^2$, together with the nitrogen atom to which they are linked, form a 5- to 8-membered ring;

$R^3$ is alkyl, aryl or aralkyl;

$R^4$ is hydrogen, alkyl, aryl or aralkyl;

"alkyl" refers to groups of up to 12 carbon atoms;

"cycloalkyl" refers to cyclic hydrocarbon groups of 3 to 12 carbon atoms;

"aryl" refers to monocyclic or bicyclic aromatic groups containing from 6 to 10 carbon atoms in the ring portion;

"cycloheteroalkyl" refers to 5-, 6- or 7-membered saturated ring that include one or two heteroatoms selected from nitrogen, oxygen and sulfur, which are linked through a carbon atom either beta or gamma to a heteroatom;

"heteroaryl" refers to 5- or 6-membered aromatic rings that include one or two heteroatoms selected from nitrogen, oxygen, and sulfur, which are not attached directly by a heteroatom to the "N" of the —NR$^1$R$^2$ group;

"cydoheteroalkylalkyl" refers to 5-, 6- or 7-membered saturated rings that include one or two heteroatoms selected from nitrogen, oxygen, and sulfur, and are linked to the "N" of the —NR$^1$R$^2$ group through a (CH$_2$)$_x$ chain wherein x is 1 to 12;

"heteroarylalkyl" refers to 5-, 6- or 7-membered aromatic rings that include one to four nitrogen and/or one or two oxygen or sulfur atoms and is linked to the "N" of the —NR$^1$R$^2$ group through a (CH$_2$)$_x$ chain wherein x is one to 12; and "5- to 8-membered ring" refers to a cycloheteroalkyl or heteroaryl group wherein the "N" of the —NR$^1$R$^2$ group is the only heteroatom.

10. A compound of claim 1, selected from the group consisting of:

[1S-[1α, 2Z, 3α, 4α]]-2-[[3-[4-[[-(4-Cyclohexylbutyl)amino]carbonyl]-2-oxazolyl]-7-oxabicyclo[2.2.1]hept-2-ylidene]methyl]benzenepropanoic acid; and 1S-[1α, 2Z, 3α, 4α]]-2-[[3-[4-[[-(4-cyclohexylbutyl)amino]carbonyl]-2-oxazolyl]-7-oxabicyclo[2.2.1]hept-2-ylidene]methyl]benzenepropanoic acid.

* * * * *

UNITED STATES PATENT AND TRADEMARK OFFICE
CERTIFICATE OF CORRECTION

PATENT NO. : 5,550,248
DATED : Aug. 27, 1996
INVENTOR(S) : Raj N. Misra

It is certified that error appears in the above-identified patent and that said Letters Patent is hereby corrected as shown below:

In the title, change "STRYL" to --STYRYL--.

In Claim 1, column 23, line 10, in the structure, please change "N" to --X--;

Claim 1, column 23, line 28, please insert "(" before wherein;

Claim 1, column 23, line 65, please change "11" to --"--.

Signed and Sealed this

Third Day of December, 1996

Attest:

BRUCE LEHMAN

*Attesting Officer*   *Commissioner of Patents and Trademarks*